(12) United States Patent
Downey et al.

(10) Patent No.: US 8,080,004 B2
(45) Date of Patent: Dec. 20, 2011

(54) LAPAROSCOPIC SURGICAL INSTRUMENT

(75) Inventors: Earl Downey, Salt Lake City, UT (US); Stephen B. Carter, Poway, CA (US); Kenneth A. Gross, Northridge, CA (US); Darrin I. Schmuckle, San Marcos, CA (US); Robson L. Splane, Jr., Valley Center, CA (US)

(73) Assignee: Earl Downey, Salt Lake City, UT (US)

( * ) Notice: Subject to any disclaimer, the term of this patent is extended or adjusted under 35 U.S.C. 154(b) by 646 days.

(21) Appl. No.: 11/259,936

(22) Filed: Oct. 26, 2005

(65) Prior Publication Data

US 2007/0093790 A1 Apr. 26, 2007

(51) Int. Cl.
*A61B 17/00* (2006.01)
(52) U.S. Cl. ............. 606/1; 606/167; 606/205; 606/210
(58) Field of Classification Search ................ 606/1, 41, 606/45–46, 48–52, 139–143, 205–207
See application file for complete search history.

(56) References Cited

U.S. PATENT DOCUMENTS

| | | | |
|---|---|---|---|
| 2,959,172 A | 11/1960 | Held | |
| 3,265,429 A | 8/1966 | Shatt | |
| 3,819,091 A | 6/1974 | Hollender | |
| 3,993,064 A | 11/1976 | McCarthy et al. | |
| 4,005,897 A | 2/1977 | Smith | |
| 4,043,323 A | 8/1977 | Komiya | |
| 4,226,239 A | 10/1980 | Polk et al. | |
| 4,369,788 A | 1/1983 | Goald | |
| 5,171,249 A | 12/1992 | Stefanchik et al. | |
| 5,217,451 A | 6/1993 | Freitas | |
| 5,258,006 A | 11/1993 | Rydell et al. | |
| 5,281,220 A | 1/1994 | Blake | |
| 5,282,817 A | 2/1994 | Hoogeboom et al. | |
| 5,318,589 A | 6/1994 | Lichtman | |
| 5,355,871 A | 10/1994 | Hurley et al. | |
| 5,368,606 A | 11/1994 | Marlow et al. | |
| 5,376,094 A | 12/1994 | Kline | |

(Continued)

OTHER PUBLICATIONS

Van Veelen, M.A., et al., "Improved usability of a new handle design for laparoscopic dissection forceps" Surgical endoscopy, Jan. 2002, pp. 201-207, vol. 16(1).

(Continued)

*Primary Examiner* — Henry M Johnson, III
*Assistant Examiner* — Lynsey Crandall
(74) *Attorney, Agent, or Firm* — Thorpe North & Western LLP

(57) ABSTRACT

A laparoscopic surgical instrument configured to be ergonomic and anthropometrically correct, the laparoscopic surgical instrument comprising: (a) an ergonomic handle configured to orient a hand of a surgeon in a functional position, the handle comprising a handle grip; (b) an actuating mechanism actuatable by a finger and supported by the handle, the actuating mechanism comprising an actuator shaft and a gearing assembly operable to displace the actuator shaft with a mechanical advantage upon actuation of a trigger by the surgeon; (c) a locking mechanism configured to lock the actuating mechanism in one of a plurality of positions, the locking mechanism comprising a release located in an anthropometrically correct position; and (d) a working shaft having a proximal end coupled to and operable with the actuator shaft, the working shaft having an elongate configuration and a distal working end configured to couple a surgical tool to be manipulated by the surgeon via the handle and the actuating mechanism to perform a surgical function.

36 Claims, 5 Drawing Sheets

U.S. PATENT DOCUMENTS

| | | | |
|---|---|---|---|
| 5,456,684 A | 10/1995 | Schmidt et al. | |
| 5,472,439 A | 12/1995 | Hurd | |
| 5,476,099 A | 12/1995 | Robinson et al. | |
| 5,480,409 A | 1/1996 | Riza | |
| 5,498,256 A | 3/1996 | Furnish | |
| 5,501,654 A | 3/1996 | Failla et al. | |
| 5,514,149 A | 5/1996 | Green et al. | |
| 5,549,623 A | 8/1996 | Sharpe et al. | |
| 5,549,636 A | 8/1996 | Li | |
| 5,571,100 A * | 11/1996 | Goble et al. | 606/41 |
| 5,577,654 A | 11/1996 | Bishop | |
| 5,603,723 A | 2/1997 | Aranyi et al. | |
| 5,611,808 A | 3/1997 | Hossain et al. | |
| 5,618,294 A | 4/1997 | Aust et al. | |
| 5,618,303 A | 4/1997 | Marlow et al. | |
| 5,626,608 A | 5/1997 | Cuny et al. | |
| 5,626,609 A | 5/1997 | Zvenyatsky et al. | |
| 5,632,764 A | 5/1997 | Beideman et al. | |
| 5,645,561 A * | 7/1997 | Smith et al. | 606/193 |
| 5,669,875 A | 9/1997 | Van Eerdenburg | |
| 5,683,362 A | 11/1997 | Rowland et al. | |
| 5,718,714 A | 2/1998 | Livneh | |
| 5,735,873 A | 4/1998 | MacLean | |
| 5,762,255 A * | 6/1998 | Chrisman et al. | 227/175.2 |
| 5,782,749 A | 7/1998 | Riza | |
| 5,782,844 A | 7/1998 | Yoon et al. | |
| 5,797,927 A * | 8/1998 | Yoon | 606/144 |
| 5,807,393 A * | 9/1998 | Williamson et al. | 606/32 |
| 5,810,806 A * | 9/1998 | Ritchart et al. | 606/45 |
| 5,830,231 A | 11/1998 | Geiges, Jr. | |
| 5,865,361 A * | 2/1999 | Milliman et al. | 227/176.1 |
| 5,868,784 A | 2/1999 | Riza | |
| 5,868,785 A * | 2/1999 | Tal et al. | 606/207 |
| 5,893,874 A | 4/1999 | Bourque et al. | |
| 5,908,436 A | 6/1999 | Cuschieri et al. | |
| 5,947,996 A * | 9/1999 | Logeman | 606/205 |
| 5,976,121 A | 11/1999 | Matern et al. | |
| 6,007,561 A | 12/1999 | Bourque et al. | |
| 6,066,102 A | 5/2000 | Townsend et al. | |
| 6,074,408 A | 6/2000 | Freeman | |
| 6,077,286 A | 6/2000 | Cuschieri et al. | |
| 6,099,537 A | 8/2000 | Sugai et al. | |
| 6,129,740 A | 10/2000 | Michelson | |
| 6,139,555 A | 10/2000 | Hart et al. | |
| 6,261,307 B1 | 7/2001 | Yoon et al. | |
| 6,299,625 B1 | 10/2001 | Bacher | |
| 6,299,630 B1 | 10/2001 | Yamamoto | |
| 6,352,532 B1 * | 3/2002 | Kramer et al. | 606/41 |
| 6,419,675 B1 * | 7/2002 | Gallo, Sr. | 606/46 |
| 6,428,530 B1 | 8/2002 | Matern et al. | |
| 6,554,828 B2 | 4/2003 | Schneiter | |
| 7,131,970 B2 * | 11/2006 | Moses et al. | 606/51 |
| 7,922,739 B2 | 4/2011 | Downey et al. | |
| 2002/0004663 A1 | 1/2002 | Gittings et al. | |
| 2002/0173813 A1 | 11/2002 | Peterson et al. | |
| 2004/0199195 A1 | 10/2004 | Dumontelle | |
| 2005/0043582 A1 | 2/2005 | Stokes | |
| 2006/0079876 A1 * | 4/2006 | Houser et al. | 606/40 |
| 2006/0241652 A1 * | 10/2006 | Doll et al. | 606/119 |
| 2007/0093856 A1 * | 4/2007 | Whitfield et al. | 606/142 |
| 2008/0039860 A1 * | 2/2008 | Trudeau | 606/99 |
| 2009/0299141 A1 | 12/2009 | Downey et al. | |

OTHER PUBLICATIONS

Van Veelen, M.A., et al., "New ergonomic design criteria for handles of laparoscopic dissection forceps" Journal of Laparoendoscopic & Advances Surgical Techniques, 2001, pp. 17-26, vol. 11, No. 1.

Reyes, D.A.G., et al., "Minimal access surgery (MAS)-related surgeon morbidity syndromes" Surgical Endoscopy, 2006, pp. 1-13, vol. 20.

Emam, T.A. et al., "Influence of handle design on the surgeon's upper limb movements, muscle recruitment, and fatigue during endoscopic suturing" Surgical endoscopy, Jul. 2001, pp. 667-672, vol. 15(7).

Matern, U. et al., "Ergonomic aspects of five different types of laparoscopic instrument handles under dynamic conditions with respect to specific laparoscopic tasks: An electronmyographic-based study", Surgical Endoscopy, 2004, pp. 1231-1241, vol. 18(8).

Downey, Earl, U.S. Appl. No. 10/551,363, filed Sep. 28, 2005.

Downey, Earl, U.S. Appl. No. 12/430,777, filed Apr. 27, 2009.

* cited by examiner

LAPAROSCOPIC SURGICAL INSTRUMENT

FIELD OF THE INVENTION

The present invention relates generally to laparoscopic surgical instruments, and more particularly to a laparoscopic surgical instrument comprising a trigger control system coupled with an ergonomic design for improved usage.

BACKGROUND OF THE INVENTION AND RELATED ART

Laparoscopic surgical instruments used for laparoscopic surgery vary significantly in design. Many previous designs for laparoscopic instruments are based on a design that is decades old, a design that was adopted to facilitate their use in upper airway endoscopy. These instruments are bent such that their handles are as much as 90 degrees out of alignment with their functional ends. These instruments were designed primarily to allow the surgeon to achieve a direct line of sight through a sheath and into the area where the instrument was intended to perform a surgical task. Because of this, the instruments were awkward and difficult to use for any extended period of time or for lengthy procedures. Moreover, they were not designed for complex internal surgical operations, such as suturing. As such, the function of these instruments largely dictated their form.

Surgical instruments incorporating a bent-handle design can be difficult to use, and can also cause injury to the surgeon. The design requires the operator to hold their wrist in awkward positions in order to manipulate the instrument. These positions are not only awkward, but they also encourage the development of carpal tunnel syndrome and chronic joint stress by positioning or orienting the hand in non-natural or non-functional positions. In attempts to alleviate often experienced pain and fatigue that are associated with use of the instrument in its intended manner, particularly in the event of long surgical procedures, many surgeons have resorted to holding the surgical instruments in a manner that is inconsistent with their design. This creates undesirable distractions, delays, and other problems during a surgical procedure.

Additionally, the bent-handle design does not efficiently translate force from the handle to the functional end of the instrument. Although the design of the instrument is intended to translate the forces that are applied to the handle to the functional end to perform a desired action, if the handle is bent out of line with the longitudinal axis of the functional end a portion of the applied force will be translated to movement of the instrument in a direction that is essentially perpendicular to this axis. This undesirable movement may be translated along the instrument to the functional end, thus compromising stability and inducing unwanted movement.

With the advent of fiber optics, the requirements for the bent handle design were largely eliminated. Rather than using a sheath to facilitate direct line of sight, surgeons today manipulate surgical instruments by means of a camera coupled to the surgical instrument that displays images onto a video screen. Given this change in technology regarding the visual aspects of surgery, it is surprising that the design of laparoscopic surgical instruments has largely remained unchanged. By utilizing modern technology, there no longer is a requirement that traditional or conventional designs be perpetuated. As such, there remains a need for a laparoscopic instrument design that is more ergonomic and simple to use.

SUMMARY OF THE INVENTION

In light of the problems and deficiencies inherent in the prior art, the present invention seeks to overcome these by providing a laparoscopic surgical instrument comprising an ergonomic design in combination with a unique trigger control or actuation system.

In accordance with the invention as embodied and broadly described herein, the present invention features a laparoscopic surgical instrument configured to be ergonomic and anthropometrically correct, the laparoscopic surgical instrument comprising: (a) an ergonomic handle configured to orient a hand of a surgeon in a functional position, the handle comprising a handle grip; (b) an actuating mechanism actuatable by a finger and supported by the handle, the actuating mechanism comprising an actuator shaft and a gearing assembly operable to displace the actuator shaft upon actuation of a trigger by the surgeon; (c) a locking mechanism configured to lock the actuating mechanism in one of a plurality of positions, the locking mechanism comprising a release located in an anthropometrically correct position; and (d) a working shaft having a proximal end coupled to and operable with the actuator shaft, the working shaft having an elongate configuration and a distal working end configured to couple a surgical tool to be manipulated by the surgeon via the handle and the actuating mechanism to perform a surgical function.

The present invention also features a laparoscopic surgical instrument specifically configured for use in surgical procedures requiring less precision and force, the laparoscopic surgical instrument comprising: (a) an ergonomic handle comprising a handle grip extending from a riser, the handle grip comprising a tubular body having a longitudinal axis oriented between 60 and 70 degrees from a longitudinal axis of the riser, the handle grip being sized and configured to orient a hand of a surgeon in a functional position; and (b) a working shaft having a proximal end supported by the riser, the working shaft having an elongate configuration and a distal working end configured to receive a surgical tool to be manipulated by the surgeon via the handle to perform a surgical function, the laparoscopic surgical instrument providing limited force generation to the working end through manipulation of the handle for improved accuracy in performing specific surgical procedures.

The present invention further features a method for facilitating performance of a surgical procedure, the method comprising: (a) providing a laparoscopic surgical instrument configured to be ergonomic and anthropometrically correct, the laparoscopic surgical instrument comprising a tubular handle having a riser and a handle grip; (b) causing the laparoscopic surgical instrument to orient a hand of a surgeon in a functional position upon grasping the handle; (c) facilitating actuation of a trigger of an actuating mechanism supported by the handle by a finger of the hand of the surgeon; (d) causing the actuating mechanism to displace a working shaft in a same direction of displacement of the trigger, the working shaft configured to couple a surgical tool to be manipulated by the surgeon via the handle and the actuating mechanism to perform a surgical function; (e) facilitating the locking of the actuating mechanism in any one of a plurality of positions; and (f) facilitating the release of the locking mechanism by a finger of the hand of the surgeon, the release being located in an anthropometrically correct position.

The present invention still further features a method for manipulating a laparoscopic surgical instrument with a single hand of a surgeon, the method comprising: (a) grasping a handle of the laparoscopic surgical instrument with a hand of a surgeon, the handle being ergonomic and anthropometrically correct to position the hand in a functional position; (b) engaging a trigger as part of an actuating mechanism supported by the handle with a single finger of the hand of the surgeon; (c) actuating the trigger in a direction with respect to the handle, thus causing the working shaft to also displace in the direction to intuitively manipulate a surgical tool operably coupled to the working shaft; (d) actuating a locking mechanism with a finger of the hand of the user to lock the actuating mechanism in one of a plurality of positions; and (e) actuating a reticulation system with a finger of the user to rotate the working shaft and the surgical tool.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying drawings in which:

DETAILED DESCRIPTION OF EXEMPLARY EMBODIMENTS

Figure 1:
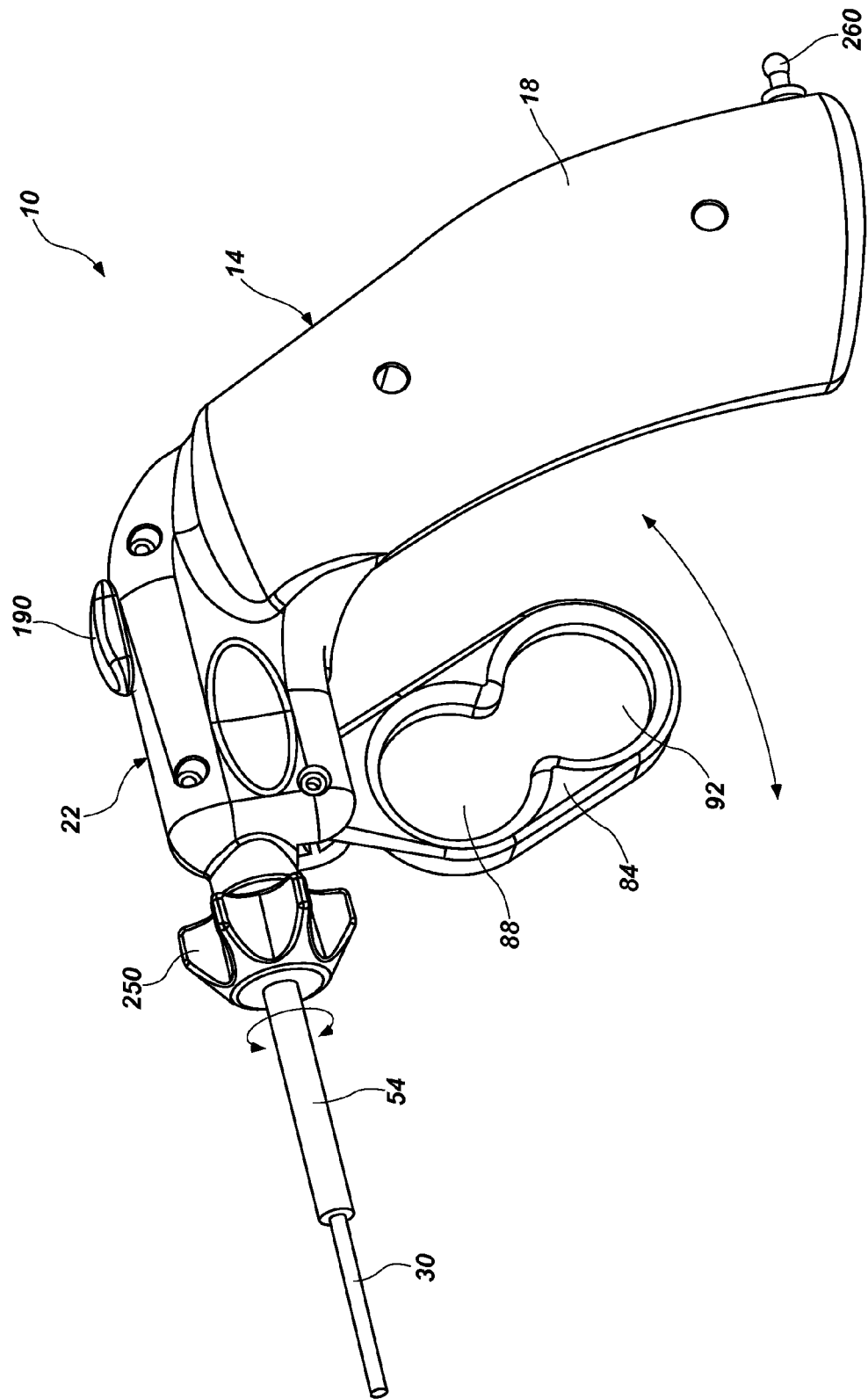
FIG. 1 illustrates a perspective view of an assembled and operable laparoscopic surgical instrument according to one exemplary embodiment of the present invention.

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention, as represented in FIGS. 1 through 5, is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

The present invention describes a method and system for providing an ergonomically and anthropometrically correct laparoscopic surgical instrument. In essence, the present invention laparoscopic surgical instrument is intended to be most applicable to the typical working endoscopic instrument. In terms of functionality, the present invention instrument is designed to perform, in an improved manner, the functions or procedures that are most typical in an endoscopic operation, such as cutting tissue, grasping tissue and structures, holding tissues and other objects such as needles, spreading tissues and structures, and so forth. In combination with the handle and the mechanisms operable therewith, the surgical tool located at the distal end of the working shaft of the instrument is capable performing all of these functions, thus making the instrument both versatile and functional. For example, the present invention instrument provides not only the force required to hold strong tissues, but also an improved degree of control, wherein the surgeon is able to sense the degree of pressure being applied.

Preliminarily, the phrase "functional position," as used herein, shall be understood to mean the well known natural or neutral orientations of the closed or semi-closed hand. One particular functional position of the hand may be identified with the wrist within 20°-30° of extension, the thumb abducted, the metacarpophalangeal joints in 15°-45° flexion, the proximal interphalangeal joints in 25°-30° flexion, and the distal interphalangeal joints in slight flexion.

The phrase "anthropometrically correct," as used herein, shall be understood to describe various actuating or functional components of the present invention surgical instrument that are located within the measurements of a hand of a surgeon, and particularly a surgeon grasping the handle of the surgical instrument, and that are operable by the surgeon in this position.

The phrase "surgical function," or "surgical procedure," as used herein, shall be understood to mean any type of activity, action, task, or motion performed by the present invention laparoscopic surgical instrument or the surgical tool coupled thereto. Examples of surgical functions include, but are not limited to, cutting or excision of tissue, clamping or grasping of tissue, and others.

The phrase "surgical tool," as used herein, shall be understood to mean any type of instrument, device, system, assembly, that attaches or couples to the working end of the working shaft of the present invention laparoscopic surgical instrument capable of performing a surgical function. Examples of surgical tools include, but are not limited to, scissors, excisors, scalpels, clamps, mirrors, lasers, lights, cameras, and others.

The present invention provides several significant advantages over prior related surgical instruments, some of which are recited here and throughout the following more detailed description. First, the present invention laparoscopic surgical instrument provides an ergonomically and anthropometrically correct design that enables the surgeon to orient his or her hand in a functional position, and to operate all mechanisms of the instrument with a single hand with minimal stress and effort. The anthropometric design provides a greater degree of control, thus allowing the surgeon to sense the degree of pressure that is being applied and to know when too much force is being exerted that may cause damage to tissue or surrounding areas. Second, the bi-directional operation and intuitive displacement of the actuating mechanism are well suited for endoscopic operating procedures. Third, the use of a second pinion gear enables both intuitive operation of the actuating mechanism and also a mechanical advantage aspect that provides for increased forces to be applied to the surgical tool through actuation of the trigger. In addition, the added pinion gear enables more delicate and precise movements due to the mechanical advantage.

Each of the above-recited advantages will be apparent in light of the detailed description set forth below, with reference to the accompanying drawings. These advantages are not meant to be limiting in any way. Indeed, one skilled in the art will appreciate that other advantages may be realized, other than those specifically recited herein, upon practicing the present invention.

With reference to FIG. 1, illustrated is a perspective view of an assembled and operable laparoscopic surgical instrument according to one exemplary embodiment of the present invention. As shown, the laparoscopic surgical instrument 10 comprises a handle 14 that is configured with a pistol-type configuration, as well as being configured to reorient the working axis of the instrument to an in-line concept. This concept avoids the up-and-down movement that occurs with prior related surgical instruments utilizing a scissor-type mechanism. In addition, these prior related instruments work the rod, which transmits the actions of the surgeon from the side. On the other hand, the present invention handle design places this action down the center of the handle and is manipulated in line by the finger of the surgeon, which is held in the functional position because of the orientation of the mechanism along the axis of the handle.

The handle 14 also provides a transfer of the dynamic actuating mechanism to a more central and intrinsic location within the handle itself, as if it really were a part of the hand. This allows a more ergonomic alignment of the actual actuating mechanism of the instrument, reducing stress on joints of the fingers and wrist. The fundamental action used to work a double action or single action surgical tool would remain unchanged. The handle could be configured to detach or rotate into a straight line, leaving a straight grasper/retractor for static functioning with a lower profile that would not tangle light and camera cords, for example.

In the exemplary embodiment shown, the handle 14 comprises a handle grip 18 configured to be grasped by a hand of a surgeon, and a riser 22, configured to extend a portion of the handle 14 away from the hand of the surgeon and to support a working rod or shaft 30 and a sleeve 54 enclosing the working shaft 30. The handle 14 is specifically configured to orient the hand of the surgeon in one or more functional positions, as such positions are commonly understood, thus providing a more natural and comfortable handle as compared to those existing in the art, as well as reducing the possibility of injury to the surgeon, which injuries may include carpal tunnel syndrome, chronic joint stress and others similar in nature.

The handle grip 18 comprises an ergonomic tubular structure designed to provide significant comfort to the surgeon, as well as to reduce fatigue and other commonly known problems associated with prior related surgical instruments. The handle grip 18 is further configured as a full hand grip that may be configured to extend beyond or below the surgeon's hand a given distance. By extending the handle grip 18 beyond the hand, the bottom of the handle grip 18 may be set on a steady rest of some sort while performing a surgical function. This is particularly useful in lengthy operations in which a certain surgical function requires precise control for an extended period of time. As will be discussed below in greater detail, the handle grip 18 is offset from the riser to provide a handle 14 that orients the surgeons' hand within a range of functional positions.

The handle 14 may be made of any material common to surgical instruments. Preferably, the handle 14 is made of a plastic or lightweight metal material. The handle 14 may further comprise some type of gripping texture formed in the handle surface to provide improved grip of the handle 14. Alternatively, the handle 14 may comprise a rubber or other material gripping element attached or otherwise incorporated into all or a portion of the handle 14.

The laparoscopic surgical instrument 10 further comprises a working shaft 30 configured to couple, and preferably releasably couple, a plurality of interchangeable surgical tools (not shown) to its distal end, and to enable the operation or function of the surgical tool with the handle 14. Essentially, the working shaft 30 is configured to translate the forces from the various components of the handle 14, such as the actuating mechanism discussed below, to the surgical tool to enable the surgical tool to function as intended. The proximal end of the working shaft 30 is supported within the riser 22 of the handle 14, thus allowing the surgeon to manipulate the surgical tool at the site of operation by manipulating the handle 14 or various components or mechanisms or systems thereof. The working shaft 30 comprises an elongate configuration and is designed to be substantially in line with an actuator shaft (not shown) used to couple the working shaft 30, as discussed below. One particular advantage of the present invention is that no part of the handle 14, and namely the hand grip 18, moves when the actuating mechanism is actuated to manipulate and operate the surgical tool coupled to the working shaft 30. This is unlike many prior related surgical tools, namely those based on an angulated scissor-type handle, wherein actuation of the scissor-type handle will cause the working shaft to move in an undesirable manner.

The working shaft 30 may be contained within a sleeve 54, as shown, which sleeve functions, among other things, to protect the working shaft 30. More specifically, the sleeve 54 functions to allow the working shaft to freely move in and out in response to trigger motion, and thus manipulate the functional end while at the same time providing for the reticulating function. The sleeve also functions as an insulator. As most instruments provide a cautery function of some kind and need to conduct an electric current to the tissues from the instrument, the sleeve insulates the working shaft so that current is conducted in a controlled or contained manner, thus eliminating random conduction, which may damage surrounding tissues near the working shaft.

Figure 2:
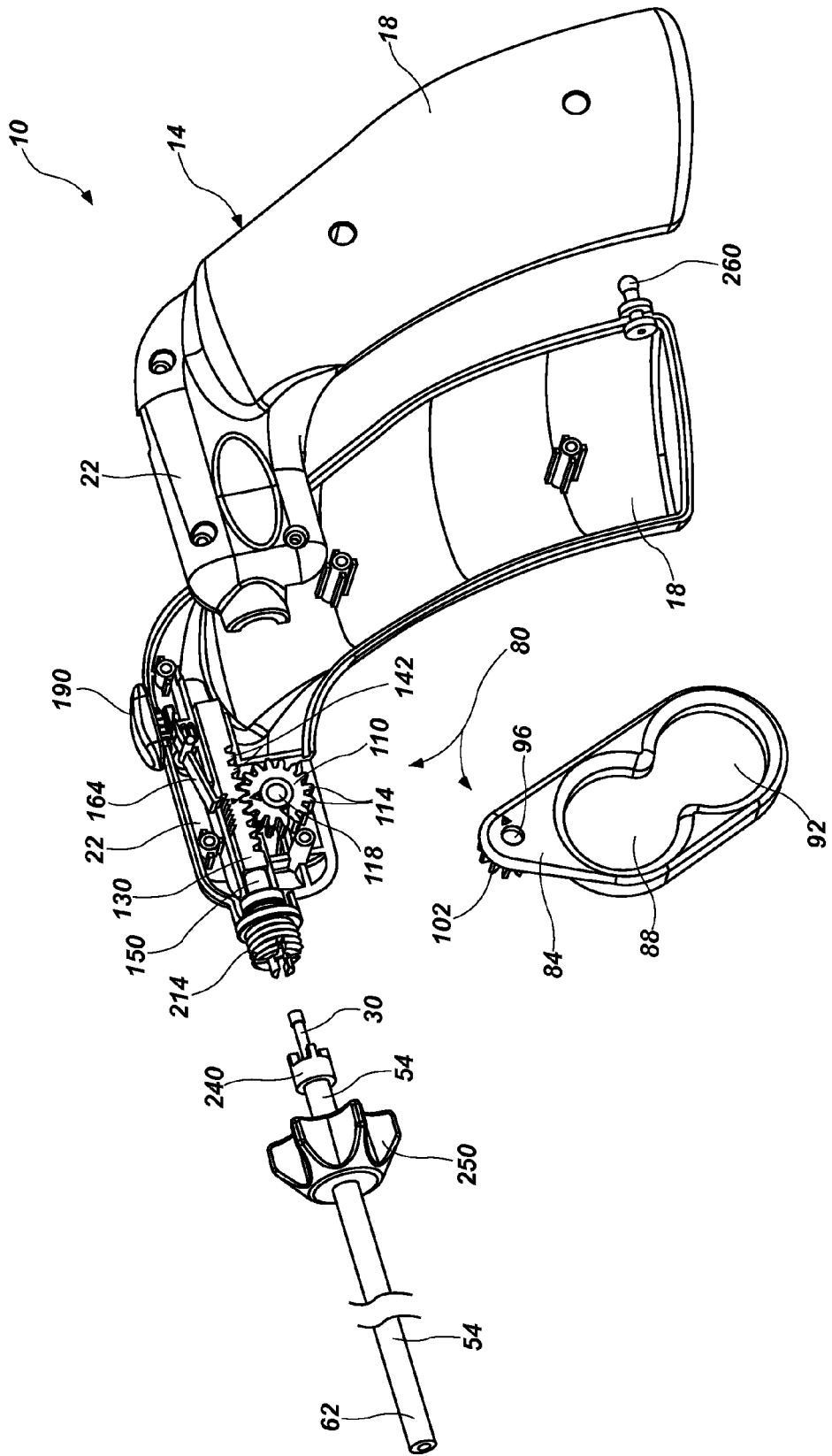
FIG. 2 illustrates a perspective view of the laparoscopic surgical instrument of FIG. 1, as partially exploded.
Figure 3:
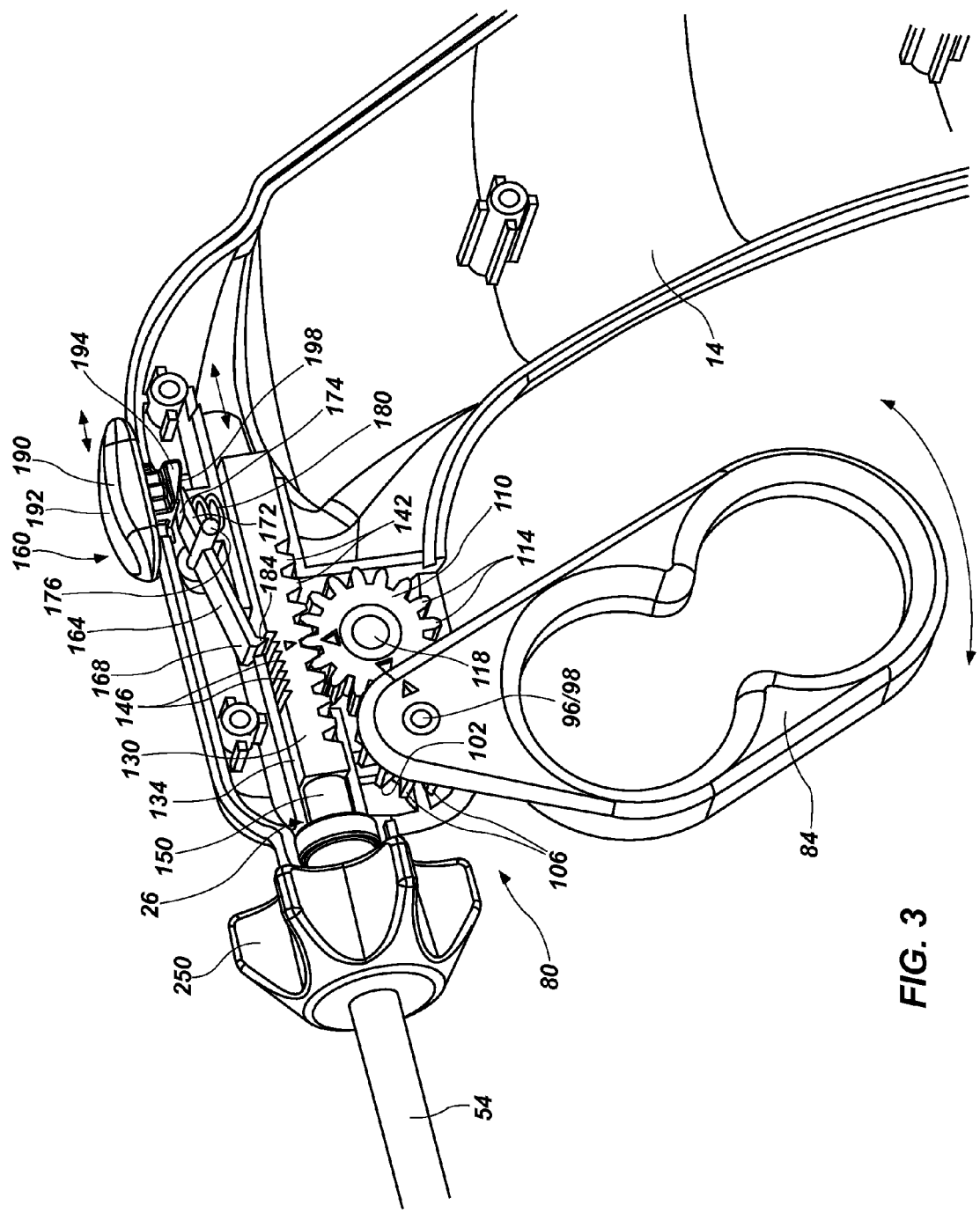
FIG. 3 illustrates a detailed cut-away perspective view of the various mechanisms and corresponding components of the laparoscopic surgical instrument of FIG. 1.

With reference to FIGS. 2 and 3, illustrated are partially exploded perspective views of the laparoscopic surgical instrument of FIG. 1 showing in more detail the internal components of the instrument. The laparoscopic surgical instrument 10 comprises an actuating mechanism 80 configured to manipulate, operate and/or actuate the surgical tool (not shown) coupled to the working shaft 30, depending upon the type of surgical tool being used. The actuating mechanism 80 is supported by the handle 14 and comprises a trigger 84 that extends away from the riser 22 of the handle 14 to be located forward of the handle grip 18, thus placing the trigger 84 in a position to be actuated using the fingers of the hand of the surgeon grasping the handle grip 18. The trigger 84 is rotatably coupled to the riser 22 using a fastener 98. The trigger 84 comprises an axis of rotation 96, or in other words is configured to rotate about pivot point 96. The actuating mechanism further comprises an actuator shaft 130 configured to displace bi-directionally within the riser 22 of the handle 14 upon actuation of the trigger 84. The actuator shaft 30 is configured to operably couple the working shaft 30, such that displacement of the actuator shaft 130 results in a corresponding displacement of the working shaft 30, which functions to control the mechanical function of the surgical tool (e.g., actuate scissors, perform a cutting operation, activate a laser, etc.)

The trigger 84 is shown as comprising first and second finger guides 88 and 92, respectively, configured to receive or accommodate the index and forefingers of the surgeon. The first and second finger guides 88 and 92 are further configured to facilitate bidirectional force from the fingers of the surgeon while simultaneously maintaining thumb, ring, and pinky finger contact on the handle grip 18 to ensure control. In other words, the trigger 84 is configured to receive both forward and backward motion of the fingers of the surgeon. Thus, the trigger 84 comprises supporting structure on both sides of the fingers as inserted into the finger guides 88 and 92. Bi-directional control allows the surgeon to open and close certain styles or types of surgical tools coupled to the working shaft 30.

The trigger 84 may further comprise a soft padded trigger insert configured to improve control of the trigger 84 by minimizing excess space between the inside surface of the finger guides 88 and 92 and the inserted fingers of the surgeon. As such, the trigger insert may be offered in different sizes to be selected by different surgeons of the laparoscopic surgical instrument 10. In addition to providing improved control, the trigger insert functions to improve comfort and reduce fatigue and stress by distributing forces over a larger surface area. This may be particularly useful in lengthy operations to reduce the incidence of cramps, fatigue, soreness or abrasions. The trigger insert may comprise a similar size and shape as the trigger 84, along with the finger guides 88 and 92. In addition, the trigger insert may be configured to removably couple to the trigger 84 using any known fastening means, such as a snap configuration, adhesives, etc.

The actuating mechanism 80 utilizes a gearing system to translate forces from the trigger 84, as applied by the finger(s) of the surgeon, to the working shaft 30, and eventually to the surgical tool attached thereto, thus providing the surgeon with control over the surgical tool attached to the working shaft 30. The gearing system is actuated by displacement or rotation of the trigger 84 about its pivot point 96. The gearing system of the actuating mechanism 80 comprises a pinion gear 102, in the form of an idler spur gear, coupled to or formed on the trigger 84. The pinion gear 102 is located on the trigger 84 such that its axis of rotation is coaxial with the axis of rotation of the trigger 84 about pivot point 96. In other words, the pinion gear 102 shares the same pivot point 96 as the trigger 84. The pinion gear 102 is not a freely rotating gear, but is instead fixed with respect to the trigger 84. Thus, the pinion gear 102 is caused to rotate only upon actuation and resulting rotation of the trigger 84.

The gearing system of the actuating mechanism 80 further comprises a rack and pinion gear combination. A pinion gear 110 is rotatably supported within the riser 22 about pivot point 118. The pinion gear 110 comprises a series of teeth 114 configured to engage and mate with a corresponding rack 142 formed in a lower surface of the actuator shaft 130. The pinion gear 110 and the idler spur pinion gear 102 function together to relate the trigger 84 to the actuator shaft 130, thereby displacing the working shaft 30 to control operation of the surgical too coupled thereto. Indeed, the idler spur pinion gear 102 comprises a series of teeth 106 annularly spaced about its perimeter, which are configured to engage and mate with the teeth 114 formed on the pinion gear 110. Therefore, actuation of the trigger 84 causes idler spur pinion gear 102 to rotate, which in turn induces a corresponding counter rotation in pinion gear 110, which in turn, induces a directional displacement of the actuator shaft 130, which displaces the working shaft 30 to control the surgical tool. The direction of displacement of the actuator shaft 130, and therefore the working shaft 30, is dependent upon the direction in which the trigger 84 is actuated. For example, looking from a point of reference viewing the laparoscopic surgical instrument 10 as oriented as shown in FIGS. 2 and 3, if the trigger 84 is caused to rotate away from the handle grip 18, this causes the idler spur pinion gear 102 to rotate counterclockwise, which induces a clockwise rotation in pinion gear 110. The clockwise rotation of pinion gear 110 causes the actuator shaft 130 and the working shaft 30 coupled thereto to also displace away from the handle grip 18. Conversely, if the trigger 84 is caused to rotate toward the handle grip 18, this causes the idler spur pinion gear 102 to rotate in a clockwise, which induces a corresponding counterclockwise rotation in pinion gear 110. The counterclockwise rotation of pinion gear 110 causes the actuator shaft 130 and the working shaft 30 to also displace toward the handle grip 18. Therefore, unlike many prior related surgical instruments, the present invention laparoscopic surgical instrument 10 provides intuitive operation by movement of the actuator shaft 130 in the same direction as the actuated trigger 84.

Due to the size and configuration of its components, the actuating mechanism 80 further provides a mechanical advantage realized between the trigger 84 and the actuator shaft 130. More specifically, the mechanical advantage enables the trigger 84 to be moved a greater distance relative to the distance that the actuator shaft 130 moves. As such, greater forces may be achieved at the surgical tool, if needed, such as might be the case in cutting, clamping, or grasping tissue. The mechanical advantage provides the surgeon with precise control of the surgical tool, in that large movement of the trigger 84 only results in small movement of the actuator shaft 130, and ultimately the working shaft 30 coupling the surgical tool. Therefore, more delicate procedures requiring greater precision than is available with prior related surgical instruments may be performed.

The mechanical advantage may be different for different instruments. Indeed, the specific mechanical advantage built into a laparoscopic surgical instrument based on the present invention may be varied by operably configuring together different components, such as gear assemblies with different gear ratios. In the exemplary embodiment shown, the mechanical advantage is about 5:1. The mechanical advantage may be configured to be less than or greater than this, but will typically range between 3:1 and 7:1. This range, however, is not to be construed as limiting. For instance, a surgical instrument may be configured with a 1.5:1 or a 10:1 mechanical advantage as well.

Another advantage of the actuation system 80 of the present invention is the minimization of the overall hand motion needed to operate the instrument. Hand motion is indeed minimized as a result of the gearing system employed, in combination with the configuration of the handle to orient the hand in a functional position. Hand motion is further minimized due to the configuration and location of the reticulation system, if employed, which is discussed in greater detail below. By minimizing hand motion, the surgeon is less prone to fatigue and mistakes or injury resulting therefrom.

The present invention laparoscopic surgical instrument 10 further comprises a locking mechanism configured to lock the actuating mechanism 80 in one of a plurality of positions. In the exemplary embodiment shown, the locking mechanism 160 is configured to interact with the actuator shaft 130 to lock the actuating mechanism 80.

More specifically, the locking mechanism 160 comprises a plurality of notches 146 formed on at least a portion of an upper surface 134 of the actuator shaft 130. A pawl 164 having a first end 168 and a second end 172 is configured to engage the notches 146 to lock the actuator shaft 130 in place and to prevent its further displacement. The notches 146 and the pawl 164 are configured to provide a ratcheting effect so that the actuator shaft 130 is capable of moving in a unidirectional manner when the pawl 164 is engaged with the actuator shaft 130. In the exemplary embodiment shown, the notches 146 and pawl 164 are each configured so that, when engaged, the actuator shaft 130 may displace toward the handle grip 18 upon squeezing the trigger 84 to displace it toward the handle grip 18. In this configuration, and with the pawl 164 engaged, the trigger 84 and actuator shaft 130 are prohibited from displacing away from the handle grip 18, thus locking them in place, as well as the working shaft 30 and any components of the surgical tool operable therewith. Other configurations are contemplated herein.

The pawl 164 may be pivotally mounted to a portion of the riser 22 and may be biased by a biasing element 180 toward an engaged position with the notches 146 formed in the actuator shaft 130. The biasing element may comprise any commonly known in the art, and is shown as preferably comprising a spring situated between a support and the lower surface of the second end 172 pawl 164. The pawl 164 is configured to pivot about pivot point 176 with the first end 168 being on one side of the fulcrum support and the second end 172 being on the opposite side. In other words, the pawl 164 is configured to teeter about the fulcrum pivot point 176.

The locking mechanism further comprises a release 190 configured to selectively release the pawl 164 from the actuator shaft 130, thus enabling the actuating mechanism 80 to move in the direction previously prohibited. The release 190 may comprise any type of release, but is preferably a quick release located in an anthropometrically correct position about the handle 14. In the exemplary embodiment shown, the release 190 comprises a thumb release located atop the riser 22. The thumb release 190 comprises an actuator 194 extending down from a button 192. The actuator 194 comprises an inclined surface 198 that is configured to engage a corresponding inclined surface 174 formed in the second end 172 of the pawl 164. In this configuration, the release 190 may be actuated by sliding the button 192 in a forward direction towards the working shaft 130. By displacing the button 192 in this direction, the actuator 194, and particularly its inclined surface 198, slides along the inclined surface 174 of the pawl 164, which causes the pawl 164 to rotate counterclockwise about the pivot point 176. The counterclockwise rotation of the pawl 164 effectively functions to overcome the biasing element 180, thus disengaging the pawl 164 from the actuator shaft 130 and allowing the actuating mechanism 80, namely the trigger 84, the pinion gears 102 and 110, and the actuator shaft 130, to move in the direction previously prohibited. This effectively allows the working shaft 30 to also move in the direction previously prohibited, to control the surgical tool as needed. By actuating the thumb release 190, the actuating mechanism 80 is allowed to displace in bi-directionally. The thumb release therefore functions to override the locking mechanism 160 when it is desired to do so.

The present invention contemplates other types of locking mechanisms for locking the actuating mechanism 80 in place. For example, rather than interacting with and locking the actuator shaft 130, thereby locking the remaining components of the actuating mechanism 80, the locking mechanism may be configured to interact with one of the pinion gears 102 and 110, or the trigger 84 itself. Such mechanisms are well known in the art.

The locking mechanism 160 functions to provide a variable position lock on the actuating mechanism and works in conjunction with the actuating mechanism 80 and its mechanical advantage. For example, the actuating mechanism 80 allows the surgeon to grasp or clamp an object using a significant amount of force and to lock the actuating mechanism in that position for any period of time. This allows the surgeon to relax his or her grip on the handle 14, while maintaining suitably strong forces on the object being grasped or clamped. As such, the surgeon is able to reduce stresses in the hand and to better concentrate on the operating procedure. In addition, the release 190 is positioned both ergonomically and anthropometrically, allowing the surgeon to actuate the release 190 with one hand while still grasping the handle 14 and actuating the trigger 84.

Figure 4:
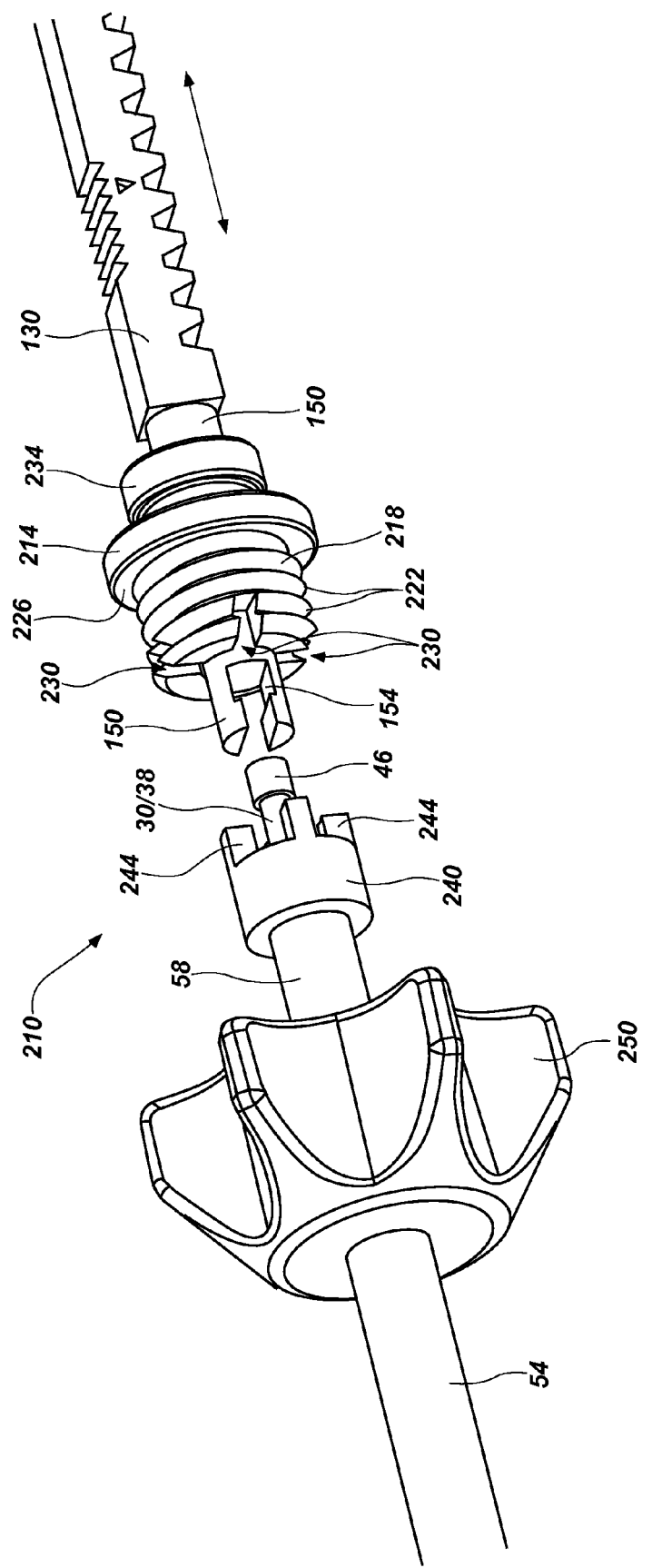
FIG. 4 illustrates a detailed, exploded perspective view of the reticulation system and the coupling configuration of the working shaft to the handle of the laparoscopic surgical instrument of FIG. 1.

With reference to FIGS. 2-4, the exemplary laparoscopic surgical instrument 10 further comprises a reticulation system 210 operable with the working shaft 30 and configured to facilitate selective rotation of the working shaft 30 (and/or the sleeve 54 enclosing the working shaft 30) and the surgical tool attached thereto. Specifically, the reticulation system 210 comprises a threaded bushing or threaded collar 214 fittable over and rotatable about a portion of the actuator shaft 130, shown as shaft extension 150. The threaded collar 214 comprises a threaded body 218 juxtaposed to and extending from a flange 226. The threaded collar 214 is supported by the riser 22 via a retaining member 234 configured to be seated within a corresponding groove 26 formed in the riser 22. The retaining member 234 may also configured to rotate within the groove 26 to enable the threaded body portion 218 to rotate, or the retaining member 234 may be seated in a fixed manner within the groove 26 and a portion thereof rotatably coupled to the threaded body 218. The threaded body 218 further comprises one or more keyholes 230 formed therein.

As discussed above, the working shaft 30 may be enclosed or encased within a sleeve, shown as sleeve 54, which sleeve may be coupled to the surgical tool along with the working shaft 30. The sleeve 54 is shown as comprising an elongate body having a proximal end 58 and a distal end 62. The proximal end 58 further comprises a key 240 having one or more key segments 244 configured to engage and mate with the key holes 230 formed in the threaded body 218 of the threaded collar 214. As such, rotation of the threaded collar 214 will induce a corresponding rotation within the sleeve 54, and thus the surgical tool coupled thereto.

To facilitate rotation of the sleeve 54 and ultimately the surgical tool coupled thereto, the reticulation system further comprises a reticulation knob 250 having a threaded bore configured to be threaded onto the threaded body 218 of the threaded collar 214 to nest against the flange 226, thereby securing the reticulation knob 250 to the collar 214. At many times during a surgical procedure there is a necessity to manipulate the surgical tool into several different orientations and positions. The reticulation system is designed to facilitate, via the reticulation knob 250, the easy, efficient, and comfortable rotation of the surgical tool. It is specifically noted herein that the reticulation knob 250 is located in both an ergonomic and anthropometrically correct position, within the reach of a finger of the surgeon, particularly the forefinger. As such, the surgeon can operate the laparoscopic surgical instrument 10 with one hand, which does not have to release the handle grip 18 to rotate the reticulation knob 250. The reticulation system may also be configured to operate electronically, such as via battery power.

FIG. 4 further illustrates a way of coupling the working shaft 30 to the handle 14, and particularly the actuator shaft 130 contained within the handle 14. This coupling configuration provides many advantages over prior related surgical instruments, namely ease of use and interchangeability. As shown, the shaft extension 150 of the actuator shaft 130 comprises, at its distal end, a coupler 154 configured to receive and couple the proximal end 38 of the working shaft 30, which has located thereon a disc or flange 46 configured to engage and seat within the coupler 154. To couple the working shaft 30 to the actuator shaft 130, the flange 46 is inserted into the coupler 154 through a slotted portion, thereby securing the rim of the flange 46 against the edge of the coupler 154. Once the flange 46 of the working shaft 30 is inserted into and seated within the coupler 154, the key 240 of the sleeve 54 is caused to engage the threaded body 218 of the collar 214. The reticulation knob 250 is then screwed in place, thus securing the coupling connection between the working shaft 30 and the actuator shaft 130. This connection configuration provides for easy interchangeability in that several different types of working shafts 30, each configured to perform a different function, may be easily and quickly interchanged with one another. In other words, several different types of working shafts may be interchanged with one another and used with a single handle, namely handle 14. To uncouple the working shaft 30, the reticulation knob 250 is simply removed, thus allowing the key 240 to disengage from the collar 214. The flange 46 may then be slid out of the coupler 154 through the slotted portion.

Referring back to FIG. 1, the laparoscopic surgical instrument 10 further comprises an electrical connector 260 supported within the handle 14. The electrical connector may be used for various purposes, such as electro-cautery functions. The electrical connector 260 is preferably located on the side of the handle grip 218 near its bottom, thus minimizing the chance for cords to interfere with one another, as well as to reduce the chance of the cords putting undesirable tension on the handle in a manner that would interfere with the proper operation of the surgical instrument.

Figure 5:
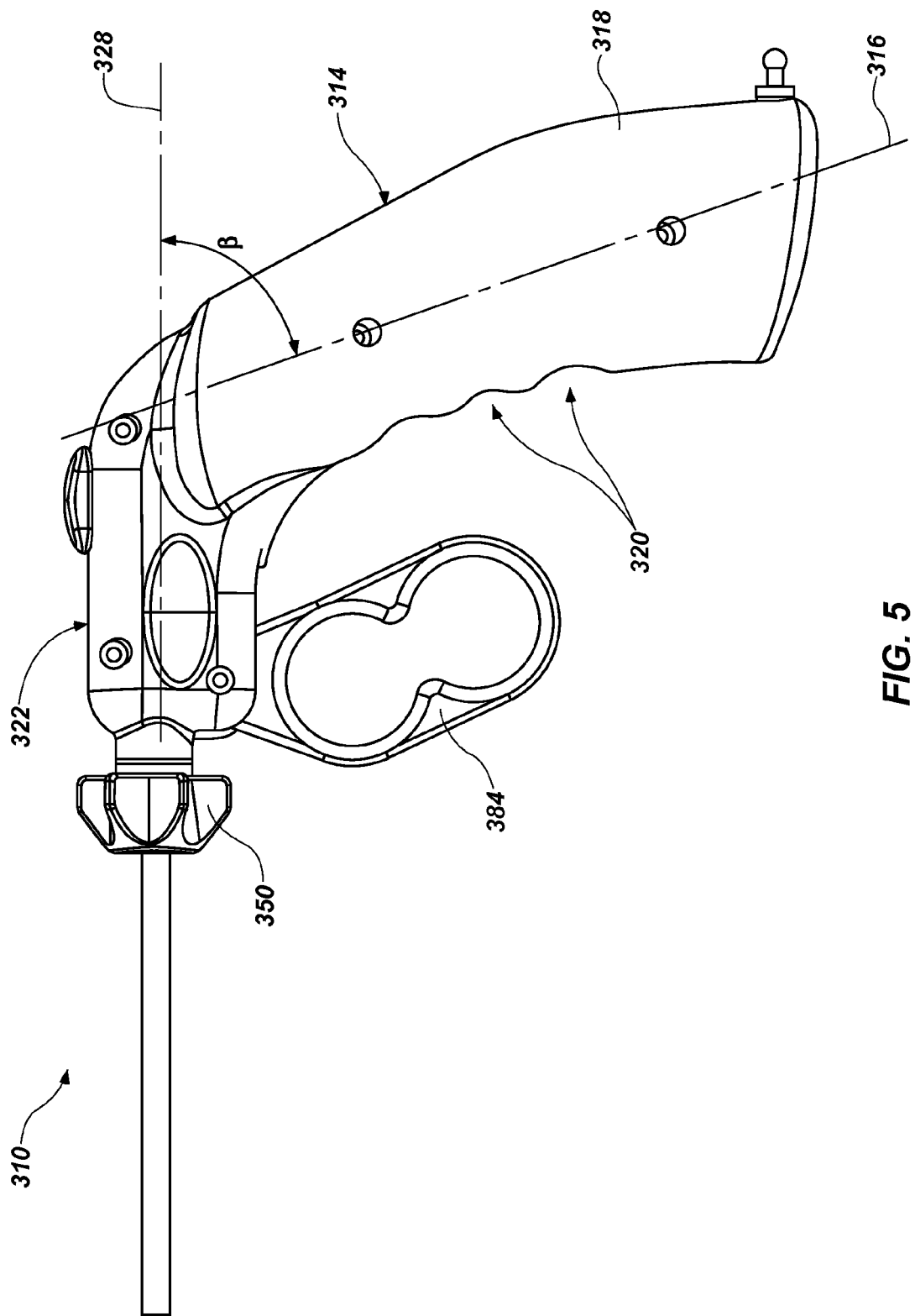
FIG. 5 illustrates a side view of a laparoscopic surgical instrument according to another exemplary embodiment of the present invention, wherein the surgical instrument does not comprise an actuating mechanism.

With reference to FIG. 5, illustrated is a side view of a laparoscopic surgical instrument according to another exemplary embodiment of the present invention. In this embodiment, the laparoscopic surgical instrument 310 comprises a similar handle 314 as the one discussed above, as well as an actuation mechanism with trigger 384. As such, the description above is incorporated herein, where applicable. However, unlike the laparoscopic surgical instrument discussed above and illustrated in FIGS. 1-4, the laparoscopic surgical instrument 310 comprises an actuating mechanism with a lesser mechanical advantage that allows the surgeon to perform a surgical procedure where greater force may cause damage to delicate tissue. For example, this particular laparoscopic surgical instrument may be particularly suited for a bowel grasping procedure. By reducing the mechanical advantage, the working end is capable of providing more sensitive operations, while still providing force multiplication. As such, the present invention contemplates laparoscopic surgical instruments with different mechanical advantages to suit different surgical needs.

FIG. 5 also illustrates the laparoscopic surgical instrument 310 as comprising a handle 314 having a handle grip 318 and a riser 322, wherein a working shaft 330 is supported by the riser 322 in a similar manner as discussed above The laparoscopic surgical instrument 310 also comprises a reticulation system similar to the one discussed above, which is configured to provide rotation to the surgical tool via the reticulation knob 350.

FIG. 5 further illustrates the orientation of the handle grip 318 with respect to the riser 322. As shown, the handle grip 318 comprises a longitudinal axis 316 that is offset a predetermined angle from a longitudinal axis 328 of the riser 322. The angle β existing between these two axis may be between 60 and 80 degrees (or between 100 and 120 degrees as measured from the working shaft), thus orienting the hand of the surgeon in a functional position. In the embodiment shown, the angle β is 68° (or 112° as measured from the working shaft). The relationship of the handle grip 318 to the riser 322 shown in FIG. 5 and discussed herein is also applicable to the handle 14 discussed above and shown in FIGS. 1-4.

The handle grip 318 may further comprise one or more finger guides formed therein, shown as finger guides 320, as commonly known in the art. These may assist the surgeon in maintaining a proper grip on the handle 314.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative exemplary embodiments of the invention have been described herein, the present invention is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are expressly recited. Accordingly, the scope of the invention should be determined solely by the appended claims and their legal equivalents, rather than by the descriptions and examples given above.

What is claimed and desired to be secured by Letters Patent is:

1. A laparoscopic surgical instrument configured to be ergonomic and anthropometrically correct, said laparoscopic surgical instrument comprising:
   an ergonomic handle comprising a riser and a handle grip that extends continuously from an uppermost surface of said riser in a rearward and downward direction, said riser extending away from an upper region of said handle grip;
   an actuating mechanism actuatable by a finger of a user and supported by said handle, said actuating mechanism comprising an actuator shaft and a gearing assembly operable to displace said actuator shaft with a mechanical advantage;
   a pivoting trigger facilitating operation of said actuating mechanism, and extending downward from a pivot point located about said riser in a forwardly offset position relative to said handle grip, wherein upon rotation towards said handle grip, a longitudinal axis of said trigger converges with a longitudinal axis of said handle grip, and wherein a continual clearance is maintained between said trigger and said handle grip throughout said rotation of said trigger, said offset position substantially correlating to a neutral orientation of said hand;

a locking mechanism configured to lock said actuating mechanism in one of a plurality of positions, said locking mechanism comprising a release operable by said user, and positioned about the riser so as to correlate to a neutral orientation of said hand; and a working shaft having a proximal end coupled to and operable with said actuator shaft, said working shaft having an elongate configuration and a distal working end configured to couple a surgical tool to be manipulated by said user via said handle and said actuating mechanism to perform a surgical function, wherein during use of the instrument, a hand of the user is maintained in a position consistent with a functional position of the hand, and wherein the laparoscopic surgical instrument provides an ergonomically and anthropometrically correct design that minimizes stress on said hand of said user.

2. The laparoscopic surgical instrument of claim 1, wherein said actuating mechanism is operable to displace said actuator shaft and said working shaft in different directions depending upon a rotational direction of said pivoting trigger.

3. The laparoscopic surgical instrument of claim 1, wherein said gearing assembly comprises a first pinion gear operable with a rack.

4. The laparoscopic surgical instrument of claim 3, further comprising a second pinion gear operable with said first pinion gear to cause said actuator shaft to be displaced in a same direction of said trigger when actuated by said user, thus providing intuitive operation of said laparoscopic surgical instrument.

5. The laparoscopic surgical instrument of claim 4, wherein said second pinion gear comprises an idler spur gear.

6. The laparoscopic surgical instrument of claim 4, wherein said second pinion gear comprises a different size than said first pinion gear to provide said mechanical advantage to said working end.

7. The laparoscopic surgical instrument of claim 3, wherein said rack is formed on at least a portion of an underside portion of said actuator shaft.

8. The laparoscopic surgical instrument of claim 1, wherein said handle grip is configured to extend a pre-determined distance below said hand of said user when grasped by said user.

9. The laparoscopic surgical instrument of claim 1, further comprising a reticulation system operable with said working shaft and configured to facilitate selective rotation of said working shaft and said surgical tool.

10. The laparoscopic surgical instrument of claim 9, wherein said reticulation system comprises:

a threaded collar fittable over and rotatable about a portion of said actuator shaft, said threaded collar comprising a keyhole formed therein;

a sleeve fittable over said working shaft and having a keyed end configured to engage said keyhole of said threaded collar; and a reticulation knob fittable onto said threaded collar at an end of said handle and within reach of a finger of said hand of said user, said reticulation knob being configured to rotate said threaded collar, and therefore said sleeve, said working shaft, and said surgical tool.

11. The laparoscopic surgical instrument of claim 10, wherein said reticulation knob is positioned anthropometrically, such that said user may operate said actuating mechanism and said reticulation system with one hand.

12. The laparoscopic surgical instrument of claim 1, wherein said pivoting trigger comprises at least one finger guide having supporting structure on both sides of the finger guide configured to receive both forward and backward motion of the finger of said user inserted into the finger guide.

13. The laparoscopic surgical instrument of claim 1, further comprising an electrical connector operably supported about said handle and configured to enable said laparoscopic surgical instrument to perform one or more electro-cautery functions.

14. The laparoscopic surgical instrument of claim 1, further comprising a trigger insert coupled to said trigger, said trigger insert configured to provide improved comfort, reduced injury, proper sizing, and improved control.

15. The laparoscopic surgical instrument of claim 14, wherein said trigger insert is removably coupled to said trigger.

16. The laparoscopic surgical instrument of claim 1, wherein said working shaft is removably coupled to said actuator shaft.

17. The laparoscopic surgical instrument of claim 1, further comprising a plurality of interchangeable surgical tools operably coupled to said distal working end of said working shaft.

18. The laparoscopic surgical instrument of claim 1, wherein said locking mechanism comprises:

a plurality of notches formed on at least a portion of an upper surface of said actuator shaft;

a pawl pivotally mounted to said handle and configured to engage said notches to lock said actuating mechanism in one of said plurality of positions, said notches and said pawl configured to provide a ratcheting function, wherein said actuating mechanism is allowed to move freely in one direction, while being prohibited to move in an opposite direction;

a biasing element configured to bias said pawl about its pivot point and to an engaged position with respect to said adjustment notches; and a thumb actuated release supported about said handle and configured to engage said pawl to overcome said biasing element to disengage said pawl from said adjustment notches, thus enabling said actuating mechanism to move in said opposite direction.

19. The laparoscopic surgical instrument of claim 18, wherein said pawl comprises a first end and a second end, said first end being configured to engage said notches and said second end comprising an inclined surface beginning at an upper surface of said pawl and extending toward a lower surface, moving away from said pivot point.

20. The laparoscopic surgical instrument of claim 19, wherein said release is slidably mounted about said handle, said release comprising an inclined actuator configured to mate with said inclined surface of said pawl, wherein by sliding said release in a given direction said inclined actuator engages said inclined surface of said pawl to pivot said pawl about said pivot point, thus causing said pawl to disengage from one of said notches, thereby allowing said actuating mechanism to freely move in any direction.

21. The laparoscopic surgical instrument of claim 18, wherein said release is located ergonomically and anthropometrically, thus enabling said user to simultaneously operate said release and said trigger and said actuating mechanism simultaneously with the same hand.

22. The laparoscopic surgical instrument of claim 1, wherein said working shaft is rotatably coupled to said actuator shaft.

23. The laparoscopic surgical instrument of claim 1, wherein said working shaft is contained within a sleeve, said sleeve being configured to facilitate reticulation and manipulation of said working end, and also to provide an insulating function to contain any current conducted through said working shaft.

24. The laparoscopic surgical instrument of claim 22, wherein said working shaft is selected from a plurality of different types of working shafts, each being interchangeable and configured to be coupled to said actuator shaft.

25. The laparoscopic surgical instrument of claim 1, wherein said working shaft is coupled to said actuating shaft via a coupling configuration comprising:
   a flange located about a proximal end of said working shaft; and
   a coupler located about a distal end of said actuating shaft, said coupler comprising a slotted portion configured to removably and rotatably receive and secure said flange of said working shaft.

26. The laparoscopic surgical instrument of claim 25, wherein said flange of said working shaft is further retained in said coupler by a reticulation knob.

27. A method for facilitating performance of a surgical procedure, said method comprising:
   providing a laparoscopic surgical instrument configured to be ergonomic and anthropometrically correct, said laparoscopic surgical instrument comprising:
      a handle having a riser and a handle grip extending continuously from an uppermost surface of said riser in a downward and rearward direction, said;
      riser extending away from an upper region of said handle; and
      a pivoting trigger of an actuating mechanism extending downward from a pivot point located about said riser in a forwardly offset position relative to said handle grip, wherein upon rotation towards said handle grip, a longitudinal axis of said trigger converges with a longitudinal axis of said handle grip and wherein a continual clearance is maintained between said trigger and said handle grip throughout said rotation of said trigger, said offset position substantially correlating to a neutral orientation of said hand,
      wherein the laparoscopic surgical instrument provides an ergonomically and anthropometrically correct design that minimizes stress on said hand of said user;
   facilitating actuation of said trigger by a finger of said hand of said user; and
   causing said actuating mechanism to displace a working shaft upon said rotation of said trigger while maintaining said hand of said user in a position consistent with a functional position of the hand, said working shaft configured to couple a surgical tool to be manipulated by said user via said handle and said actuating mechanism to perform a surgical function.

28. The method of claim 27, further comprising facilitating the locking of said actuating mechanism in any one of a plurality of positions.

29. The method of claim 28, further comprising facilitating the release of said locking mechanism by a finger of said hand of said user, said release being located in an anthropometrically correct position.

30. The method of claim 27, further comprising facilitating the interchangeability of said working shaft with a plurality of different types of working shafts.

31. The method of claim 30, wherein said facilitating the interchangeability comprises:
   providing a flange in a proximal end of said plurality of working shafts; and
   facilitating the releasable coupling of said flange to a coupler formed in one of said handle or a component supported therein.

32. The method of claim 27, further comprising configuring said actuation mechanism to provide a mechanical advantage to said working end.

33. A method for manipulating a laparoscopic surgical instrument with a single hand of a user to perform a surgical function, said method comprising:
   grasping a handle of said laparoscopic surgical instrument, said handle being ergonomic and anthropometrically correct to position a hand of a user in a position consistent with a functional position of said hand, and said handle having a riser and a handle grip extending continuously from an uppermost surface of said riser in a rearward and downward direction, said riser extending away from an upper region of said handle grip;
   engaging a pivoting trigger configured as part of an actuating mechanism supported about said handle and said riser with a finger of said hand of said user, said trigger extending downward from a pivot point located about said riser in a forwardly offset position relative to said handle grip, wherein upon rotation towards said handle grip, a longitudinal axis of said trigger converges with a longitudinal axis of said handle grip and wherein a continual clearance is maintained between said trigger and said handle grip throughout said rotation of said trigger, said offset position substantially correlating to a neutral orientation of said hand;
   actuating said trigger in a direction with respect to said handle grip, thus causing a working shaft to also displace in said direction to intuitively manipulate a surgical tool operably coupled to a working end of said working shaft;
   actuating a locking mechanism with a finger of said hand of said user to lock said actuating mechanism in one of a plurality of positions, said locking mechanism positioned about the riser so as to correlate to a neutral orientation of said hand; and
   actuating a reticulation system with a finger of said user to rotate said working shaft and said surgical tool,
   wherein the laparoscopic surgical instrument provides an ergonomically and anthropometrically correct design that minimizes stress on said hand of said user.

34. The method of claim 33, further comprising providing a mechanical advantage ranging from 1.5:1 and 10:1 to said working end through said actuation mechanism.

35. A laparoscopic surgical instrument configured to be ergonomic and anthropometrically correct, said laparoscopic surgical instrument comprising:
   a handle comprising a riser and a handle grip extending continuously in a rearward and downward direction from an uppermost surface of said riser, and said riser extending away from an upper region of said handle grip;
   an actuating mechanism supported by said riser, said actuating mechanism comprising:
      an actuator shaft located within said riser;
      a gearing assembly operable to displace said actuator shaft; and
      a trigger extending downwardly from a distal end of said riser to rotate about a pivot point, said trigger and said actuating mechanism being actuatable in both directions by at least one finger of a user to displace said actuator shaft in both directions and wherein upon rotation towards said handle grip, a longitudinal axis of said trigger converges with a longitudinal axis of said handle grip and wherein a continual clearance is maintained between said trigger and said handle grip throughout said rotation of said trigger, said offset position substantially correlating to a neutral orientation of said hand; and a working shaft having a proximal end coupled to and operable with said actuator shaft, and a distal working end configured to couple a surgical tool, wherein during use of the instrument, said hand of said user is maintained in a position consistent with a functional position of the hand and wherein said laparoscopic surgical instrument provides an ergonomically and anthropometrically correct design that minimizes stress on said hand of said user.

36. The laparoscopic surgical instrument of claim 1, wherein said handle grip comprises a tubular body having a longitudinal axis oriented between 60 and 80 degrees from a longitudinal axis of said riser.

* * * * *